United States Patent
Rosario-Jansen et al.

(10) Patent No.: US 9,377,454 B2
(45) Date of Patent: Jun. 28, 2016

(54) METHODS AND KITS FOR PREDICTING INFUSION REACTION RISK AND ANTIBODY-MEDIATED LOSS OF RESPONSE BY MONITORING SERUM URIC ACID DURING PEGYLATED URICASE THERAPY

(75) Inventors: Theresa Rosario-Jansen, Raleigh, NC (US); David Erick Wright, Ramona, CA (US)

(73) Assignee: CREALTA PHARMACEUTICALS LLC, Lake Forest, IL (US)

( * ) Notice: Subject to any disclaimer, the term of this patent is extended or adjusted under 35 U.S.C. 154(b) by 0 days.

(21) Appl. No.: 13/379,704

(22) PCT Filed: Jun. 25, 2010

(86) PCT No.: PCT/US2010/040082
§ 371 (c)(1),
(2), (4) Date: Aug. 8, 2012

(87) PCT Pub. No.: WO2010/151823
PCT Pub. Date: Dec. 29, 2010

(65) Prior Publication Data
US 2012/0301454 A1    Nov. 29, 2012

Related U.S. Application Data

(60) Provisional application No. 61/269,669, filed on Jun. 25, 2009, provisional application No. 61/248,698, filed on Oct. 5, 2009, provisional application No. 61/298,718, filed on Jan. 27, 2010.

(51) Int. Cl.
*C12Q 1/62* (2006.01)
*G01N 33/53* (2006.01)
*G01N 33/68* (2006.01)

(52) U.S. Cl.
CPC ........ *G01N 33/5308* (2013.01); *G01N 33/6893* (2013.01); *G01N 2800/107* (2013.01); *G01N 2800/52* (2013.01); *G01N 2800/56* (2013.01)

(58) Field of Classification Search
CPC .......... G01N 33/5308; G01N 33/6893; G01N 2800/107; G01N 2800/52; G01N 2800/56; A61K 38/44; A61K 47/48; C12Y 107/3003
See application file for complete search history.

(56) References Cited

U.S. PATENT DOCUMENTS

| | | |
|---|---|---|
| 5,653,974 A | 8/1997 | Hung et al. |
| 6,576,235 B1 | 6/2003 | Williams et al. |
| 6,783,965 B1 | 8/2004 | Sherman et al. |
| 7,056,713 B1 | 6/2006 | Hershfield et al. |
| 7,723,089 B2 | 5/2010 | Williams et al. |
| 7,811,800 B2 | 10/2010 | Hartman et al. |
| 7,927,589 B2 | 4/2011 | Williams et al. |
| 7,927,852 B2 | 4/2011 | Sherman et al. |
| 7,964,381 B2 | 6/2011 | Hartman et al. |
| 8,034,594 B2 | 10/2011 | Hartman et al. |
| 8,067,553 B2 | 11/2011 | Williams et al. |
| 8,148,123 B2 | 4/2012 | Hartman et al. |
| 8,178,334 B2 | 5/2012 | Hartman et al. |
| 8,188,224 B2 | 5/2012 | Hartman et al. |
| 8,293,228 B2 | 10/2012 | Hartman et al. |
| 8,465,735 B2 | 6/2013 | Hartman et al. |
| 8,541,205 B2 | 9/2013 | Hartman et al. |
| 2007/0274977 A1* | 11/2007 | Hartman et al. ............. 424/94.4 |
| 2008/0145876 A1 | 6/2008 | Armstrong et al. |

FOREIGN PATENT DOCUMENTS

| | | |
|---|---|---|
| CN | 101168052 A | 4/2008 |
| WO | 2006110819 A2 | 10/2006 |

OTHER PUBLICATIONS

Prevent—definition by Merriam-Webster online dictionary; at the web http://www.merriam-webster.com/dictionary/prevent-pp. 1-3, accessed on Jun. 27, 2013.*
Garay R.P. et al., Expert Opinion—"Antibodies against polyethylene glycol in healthy subjects and in patients treated with PEG-conjugated agents", Expert Opin. Drug Deliv., 2012, vol. 9, No. 11, pp. 1319-1323.*
FDA—Drug Safety Brochure—2012—Published on the web for Krystexxa, ref ID 3116893 at—http://www.accessdata.fda.gov/drugsatfda_docs/label/2012/125293s034lbl.pdf; total pp. 1-14.*
Sundy et al., Efficacy and Tolerability of Pegloticase for the Treatment of Chronic Gout in Patients Refractory to Conventional Treatment: Two Randomized Controlled Trials, JAMA, Aug. 17, 2011, vol. 306, No. 7, pp. 711-720.*
Buch M.H. et al., Shortening infusion times for infliximab administration, Letters to the Editor, Rheumatology, 2006, vol. 45, pp. 485-486.*
Augustsson J. et al., Low-dose glucocorticoid therapy decreases risk for treatment-limiting infusion reaction to infliximab in patients with rheumatoid arthritis, Extended Report, Ann. Rheum. Dis., 2007, vol. 66, pp. 1462-1466.*
Sundy et al., Reduction of Plasma Urate Levels Following Treatment with Multiple Doses of Pegloticase (Polyethylene Glycol? Conjugated Uricase) in Patients with Treatment-Failure Gout., Arth. Rheum., Sep. 9, 2008, vol. 58 No. 9 pp. 2882-2891, especially abstract, p. 2883 right col. paragraph 3, p. 2884 left col. paragraph 3, p. 2885 right col., paragraph 2, p. 2886 Fig. 1A, p. 2890 right col. paragraph 1.
Hamburger et al., Arthritis Advisory Committee Meeting, Pegloticase (Krystexxa) IV Infusion (online) Jun. 16, 2009, pp. 1-155 (retrieved Aug. 4, 2010), available on the internet : <URL: http://www.fda.gov/downloads/AdvisoryCommittees/CommitteesMeetingMaterials/Drugs/ArthritisDrugsAdvisoryCommittee/UCM167777.pdf> especially pp. 108-115.

(Continued)

*Primary Examiner* — Satyendra K Singh
(74) *Attorney, Agent, or Firm* — Lando & Anastasi, LLP

(57) ABSTRACT

Methods and kits for predicting infusion reaction risk and antibody-mediated loss of response during intravenous PEGylated uricase therapy in gout patients is provided. Routine SUA monitoring can be used to identify patients receiving PEGylated uricase who may no longer benefit from treatment and who are at greater risk for infusion reactions.

6 Claims, 6 Drawing Sheets

(56) References Cited

OTHER PUBLICATIONS

Sherman et al., PEG-Uricase in the Management of Treatment-Resistant Gout and Hyperuricemia Adv., Drug Deliv., Rev:, Jan. 3, 2008; vol. 60, No. 1; pp. 59-68.
International Search Report Application No. PCT/US2010/040082, Dated Aug. 19, 2010.
Ganson et al.: "Control of hyperuricemia in subjects with refractory gout, and induction of antibody against poly (ethylene glycol) (PEG), in a phase I trial of subcutaneous PEGylated urate oxidase." Arthritis Research & Therapy (2006), vol. 8, No. 1, pp. 1-10, Especially p. 4, fig. 1.
Sundy et al.: "Pharmacokinetics and Pharmacodynamics of Intravenous PEGylated Recombinant Mammalian Urate Oxidase in Patients With Refractory Gout." Arth. Rheum. (2007), vol. 56, No. 3, pp. 1021-1028. Especially p. 1024, fig 1A.
Singapore Search Report, Application No. 201109356-4, Date of Mailing Feb. 15, 2013.
Singapore Search Report, dated Feb. 15, 2013.
EP Supplementary Search Report dated Oct. 10, 2013.
Ganson, N.J. et al., "Conrtol of hyperuricemia in subjects with refractory gout, and induction of antibody against poly(ethylene glycol)(PEG), in a phase I trial of subcutaneous PEGylated urate oxidase." Arthritis Research & Therapy, vol. 8, No. 1, 2006, pp. 1-10.
Ganson, Nancy J., "Control of Hyperuricemia in Subjects with Refractory Gout, and Induction of Antibody Against Poly(ethylene Glycol)(PEG), in a Phase I Trial of Subcutaneous PEGylated Urate Oxidase", Arthritis Res Ther, 8(1): R12, 2005.
Hamburger, S. et al., "Pegloticase IV Infusion" Arthritis Advisory Committee Meeting, Jun. 16, 2009, pp. 1-155.
Hamburger, S., et al. Transcript of oral presentation entitled: "Pegloticase (Krystexxatm) IV infusion," pp. 28-213 U.S. Food and Drug Administration, Center for Drug Evaluation and Research, Arthritis Advisory Committee meeting, Jun. 16, 2009.
International Preliminary Report on Patentability for PCT/US2010/040082 dated Jan. 4, 2012.
Kelly, Susan J. et al., "Diabetes Insipidus in Uricase-Deficient Mice: A Model for Evaluating Therapy with Poly (Ethylene Glycol)-Modified Uricase", J Am Soc Nephrol 12:1001-1009, 2001.
Sherman, et al., "PEG-uricase in the management of treatment-resistant gout and hyperuricemia" Adv. Drug Deliv. Rev, 60, pp. 59-68, 2008.
Sundy, et al., "Reduction of Plasma Urate Levels Following Treatment with Multiple Doses of Pegloticase in Patients with Treatment-Failure Gout" Arthritis & Rheumatism, vol. 58, No. 9, p. 2882-2891, 2008.
Sundy, J.S. et al., "Pharmacokinetics and Pharmacodynamics of Intravenous PEGylated Recombinant Mammalian Urate Oxidase in Patients With Refractory Gout." (2007) Arth. Rheum., vol. 56, No. 3, pp. 1021-1028.
U.S. Appl. No. 60/670,573, filed Apr. 11, 2005.
Schumacher et al., "Effects of Febuxostat Versus Allopurinol and Placebo in Reducing Serum Urate in Subjects with Hyperuricemia and Gout: A 28-Week, Phase III, Randomized, Double-Blind, Parallel-Group Trial", Arthritis & Rheumatism (Arthritis Care & Research), vol. 59, No. 11, pp. 1540-1548, Nov. 15, 2008.

\* cited by examiner

METHODS AND KITS FOR PREDICTING INFUSION REACTION RISK AND ANTIBODY-MEDIATED LOSS OF RESPONSE BY MONITORING SERUM URIC ACID DURING PEGYLATED URICASE THERAPY

CROSS REFERENCE TO RELATED APPLICATIONS

This application is the United States national phase filing of the corresponding international application number PCT/US2010/040082, filed on Jun. 25, 2010, which claims priority to and benefit of U.S. Provisional Application No. 61/269,669, filed on Jun. 25, 2009, U.S. Provisional Application No. 61/248,698, filed on Oct. 5, 2009, and U.S. Provisional Application No. 61/298,718, filed on Jan. 27, 2010 which application is hereby incorporated by reference in their entirety.

FIELD OF THE INVENTION

This invention relates to methods for monitoring immunogenicity and infusion reactions during PEGylated uricase therapy.

BACKGROUND OF THE INVENTION

Throughout this application, various publications are referenced within the text. The disclosure of these publications in their entireties are hereby incorporated by reference into this application in order to more fully describe the state of the art as known to those skilled in therein as of the date of the invention described and claimed herein.

Gout is a chronic disorder of urate metabolism resulting in deposition of monosodium urate crystals in the joints and soft tissues, with accompanying inflammation and eventually, in some patients, destructive, chronic arthropathy. Gout is the most prevalent form of arthritis in men and is increasing in incidence and prevalence among older persons of both genders. Chronic gout refractory to Conventional Therapy (GRT) is an uncommon but severe outcome of progressive gout resulting from demonstrated intolerance of or refractoriness to available therapy to prevent urate crystal deposition by reducing and maintaining serum urate levels in a subsaturating range.

Elevated serum urate is a hallmark biochemical marker of gout. Persistently elevated plasma uric acid (PUA) or serum uric acid (SUA) levels result in deposition of uric acid in joints and soft tissues. As the total body burden of uric acid increases, signs and symptoms of gout result, including arthritis, characterized by recurrent painful gout flares, development of tophi and joint deformities with resultant chronic pain/inflammation and consequent loss of physical function.

The efficacy end point of successful PEGylated uricase therapy is normalization of serum uric acid levels in CGR patients while maintaining low immunogenicity profile and low risk of infusion reactions associated with intravenous injections of PEGylated uricase. However, given that the loss of PEGylated uricase effect and infusion reactions can accompany PEGylated uricase administration, clinicians should be advised as to the proper time point at which to discontinue therapy. Thus, there is a need in the art for new methods to guide clinicians when to discontinue the PEGylated uricase therapy in order to minimize infusion reactions and their associated safety risks.

SUMMARY OF THE INVENTION

The present invention provides for methods of preventing infusion reactions during PEGylated uricase therapy in a patient comprising the steps of a) administering to said patient PEGylated uricase; b) obtaining a biological sample from said patient; c) determining uric acid levels in said biological sample; and d) indicating that therapy may be discontinued to prevent infusion reactions when said uric acid level is more than about 4 mg/dl. In one aspect of the invention, PEGylated uricase therapy may be discontinued when said uric acid level is more than about 5 mg/dl. In another aspect of the invention, PEGylated uricase therapy may be discontinued when said uric acid level is more than about 6 mg/dl and in yet another aspect of the invention, the PEGylated uricase therapy may be discontinued when said uric acid level is more than about 7 mg/dl.

In another aspect of the invention, the PEGylated uricase is administered at a dosage of about 8 mg every 2 weeks. In one embodiment, the PEGylated uricase is administered at a dosage of about 8 mg every 3 weeks. In another embodiment, the PEGylated uricase is administered at a dosage of about 8 mg every 4 weeks. In yet another embodiment, the PEGylated uricase is administered at a dosage of about 4 mg every 2 weeks. In yet another embodiment, the PEGylated uricase is administered at a dosage of about 12 mg every 4 weeks.

The methods of the present invention provides for biological sample selected from the group consisting of blood, serum and plasma. In one embodiment, said uric acid levels in said biological sample are determined at least 2 hours after administration as defined in step (a). In another embodiment, said uric acid levels in said biological sample are determined at least 6 hours after administration as defined in step (a). In yet another embodiment, said uric acid levels in said biological sample are determined at least 24 hours after administration as defined in step (a). In yet another embodiment, said uric acid levels in said biological sample are determined 2 weeks after administration as defined in step (a). And in yet another embodiment, said uric acid levels in said biological sample are determined 4 weeks after administration as defined in step (a).

The methods of the present invention relate to patients suffering from gout. In one embodiment, said gout is refractory. In another embodiment, said gout is chronic or tophaceous. In yet another embodiment, the PEGylated uricase is administered intraveneously.

The methods of the present invention predict whether a patient treated with PEGylated uricase will develop infusion reaction, wherein the method comprises the steps of: a) administering to said patient PEGylated uricase; b) obtaining a biological sample from said patient; c) determining uric acid levels in said biological sample; and d) indicating that uric acid level is associated with a lower likelihood of infusion reaction when said level is maintained at less than about 4 mg/dl or indicating that said determined uric acid level is associated with a higher likelihood of infusion reaction at a time point when said level is measured at least about 4 mg/dl.

In one aspect of the invention, said uric acid level is associated with a lower likelihood of infusion reaction when said level is maintained at less than about 5 mg/dl or said determined uric acid level is associated with a higher likelihood of infusion reaction at a time point when said level is measured at least about 5 mg/dl. In another aspect of the invention, said uric acid level is associated with a lower likelihood of infusion reaction when said level is maintained at less than about 6 mg/dl or said determined uric acid level is associated with a higher likelihood of infusion reaction when said level is measured at least about 6 mg/dl. In yet another aspect of the invention, said uric acid level is associated with a lower likelihood of infusion reaction when said level is maintained at less than about 7 mg/dl or said uric acid level is associated with a higher likelihood of infusion reaction at a time point when said uric acid level is measured at least about 7 mg/dl.

In another aspect of the invention, the uric acid levels in said biological sample are determined at least 3 days after the administration as defined in step (a). In another aspect of the invention, the uric acid levels in said biological sample are determined at least 1 week after the administration as defined in step (a). In another aspect of the invention, the uric acid levels in said biological sample are determined at least 2 weeks after the administration as defined in step (a). In another aspect of the invention, the uric acid levels in said biological sample are determined at least 4 weeks after the administration as defined in step (a).

The methods of the present invention predict whether a patient treated with PEGylated uricase will develop antibody-mediated PEGylated uricase clearance without measuring anti-PEGylated uricase and anti-PEG antibodies titer, wherein the method comprises the steps of a) administering to said patient PEGylated uricase; b) obtaining a biological sample from said patient; c) determining uric acid levels in said biological sample; and d) indicating that uric acid level is associated with a lower likelihood of antibody-mediated PEGylated uricase clearance when said level is maintained at less than about 4 mg/dl or indicating that said determined uric acid level is associated with a higher likelihood of antibody-mediated PEGylated uricase clearance at a time point when said uric acid level is measured at least about 4 mg/dl.

In one aspect of the invention, said uric acid level is associated with a lower likelihood of antibody-mediated PEGylated uricase clearance when said level is maintained at less than about 5 mg/dl or indicating that said determined uric acid level is associated with a higher likelihood of antibody-mediated PEGylated uricase clearance at a time point when said uric acid level is measured at least about 5 mg/dl. In another aspect of the invention, said uric acid level is associated with a lower likelihood of antibody-mediated PEGylated uricase clearance when said level is maintained at less than about 6 mg/dl or indicating that said determined uric acid level is associated with a higher likelihood of antibody-mediated PEGylated uricase clearance at a time point when said uric acid level is measured at least about 6 mg/dl. In yet another aspect of the invention, said uric acid level is associated with a lower likelihood of antibody-mediated PEGylated uricase clearance when said level is maintained at less than about 7 mg/dl or indicating that said determined uric acid level is associated with a higher likelihood of antibody-mediated PEGylated uricase clearance at a time point when said uric acid level is measured at least about 7 mg/dl.

In another aspect of the invention, the uric acid levels in said biological sample are determined at least 3 days after the administration as defined in step (a). In another aspect of the invention, the uric acid levels in said biological sample are determined at least 1 week after the administration as defined in step (a). In another aspect of the invention, the uric acid levels in said biological sample are determined at least 2 weeks after the administration as defined in step (a). In another aspect of the invention, the uric acid levels in said biological sample are determined at least 4 weeks after the administration as defined in step (a).

DETAILED DESCRIPTION OF THE INVENTION

Definitions

Figure 1:
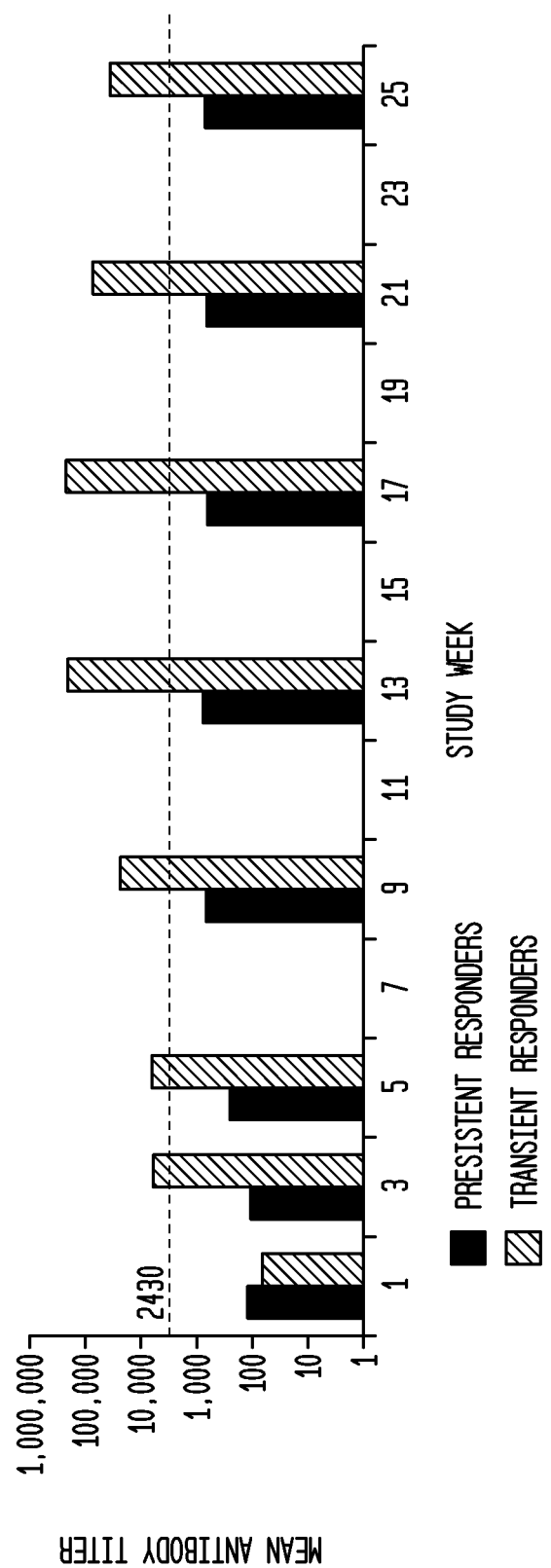
FIG. 1 shows mean anti-pegloticase antibody titer in patients receiving pegloticase every 2 Weeks.

In accordance with this detailed description, the following abbreviations and definitions apply. It must be noted that as used herein, the singular forms "a," "an," and "the" include plural referents unless the context clearly dictates otherwise.

It had been surprisingly discovered that monitoring SUA levels predicts antibody-mediated loss of response and the majority of infusion reactions during PEGylated uricase therapy. It has been found that most infusion reactions occurred after loss of SUA response. Therefore, routine monitoring of SUA can be used to prospectively identify patients receiving PEGylated uricase who no longer benefit from treatment and are at a greater risk for infusion reactions.

The term "therapeutic efficacy" as used herein refers to the effectiveness of a particular treatment regimen. Specifically, therapeutic efficacy is defined by achieving serum urate levels less or about 6 mg/dl. This includes a balance of efficacy, toxicity (e.g., side effects and patient tolerance of a formulation or dosage unit), patient compliance, and the like.

The terms "treating," "treatment," and the like are used herein to refer to obtaining a desired pharmacological and physiological effect. The effect can be prophylactic in terms of preventing or partially preventing a disease, symptom, or condition thereof and/or can be therapeutic in terms of a partial or complete cure of a disease, condition, symptom, or adverse effect attributed to the disease. The term "treatment," as used herein, covers any treatment of a disease in a mammal, such as a human, and includes: (a) preventing the disease from occurring in a patient which can be predisposed to the disease but has not yet been diagnosed as having it, i.e., causing the clinical symptoms of the disease not to develop in a patient that can be predisposed to the disease but does not yet experience or display symptoms of the disease; (b) inhibiting the disease, i.e., arresting or reducing the development of the disease or its clinical symptoms; and (c) relieving the disease, i.e., causing regression of the disease and/or its symptoms or conditions. Treating a patient's suffering from disease related to pathological inflammation is contemplated. Preventing, inhibiting, or relieving adverse effects attributed to pathological inflammation over long periods of time and/or are such caused by the physiological responses to inappropriate inflammation present in a biological system over long periods of time are also contemplated.

As used herein the term "immunogenicity" refers to the induction of an immune response by an injected preparation of PEG-modified or unmodified uricase (the antigen), while "antigenicity" refers to the reaction of an antigen with preexisting antibodies. Collectively, antigenicity and immumunogenicity are referred to as "immunoreactivity." In previous studies of PEGylated uricase, immunoreactivity is assessed by a variety of methods, including: 1) the reaction in vitro of PEGylated uricase with preformed antibodies; 2) measurements of induced antibody synthesis; and 3) accelerated clearance rates of PEGylated uricase after repeated injections.

As used herein the term "infusion reaction" is an undesired and unintended effect of a PEGylated uricase occurring within 2 hours after the PEGylated uricase or placebo infusion that cannot be reasonably attributed to another cause. In particular, an adverse drug reaction occurs at doses used for prophylaxis, diagnosis, or therapy.

The PEGylated uricase conjugates of the present invention are useful for lowering the levels of uric acid in the body fluids and tissues of mammals, preferably humans, and can thus be used for treatment of elevated uric acid levels associated with conditions including gout, tophi, renal insufficiency, organ transplantation and malignant disease. PEGylated uricase conjugates can be injected into a mammal having excessive uric acid levels by any of a number of routes, including intravenous, subcutaneous, intradermal, intramuscular and intraperitoneal routes.

In one embodiment, PEGylated uricase is administered in a pharmaceutically acceptable excipient or diluent at 8 mg every two weeks. In another embodiment, PEGylated uricase can be administered at 8 mg every four weeks. In yet another embodiment, PEGylated uricase can be administered at 8 mg every three weeks.

In the other aspect of the invention, PEGylated uricase can be administered at 4 mg every two weeks. In yet another aspect of the invention, PEGylated uricase can be administered at 12 mg every four weeks.

Pharmaceutical formulations containing PEGylated uricase can be prepared by conventional techniques, e.g., as described in Gennaro, A R (Ed.) (1990) Remington's Pharmaceutical Sciences, 18th Edition Easton, Pa.: Mack Publishing Co. Suitable excipients for the preparation of injectable solutions include, for example, phosphate buffered saline, lactated Ringer's solution, water, polyols and glycerol. Pharmaceutical compositions for parenteral injection comprise pharmaceutically acceptable sterile aqueous or non-aqueous liquids, dispersions, suspensions, or emulsions as well as sterile powders for reconstitution into sterile injectable solutions or dispersions just prior to use. These formulations can contain additional components, such as, for example, preservatives, solubilizers, stabilizers, wetting agents, emulsifiers, buffers, antioxidants and diluents.

PEGylated uricase can also be provided as controlled-release compositions for implantation into an individual to continually control elevated uric acid levels in body fluids. For example, polylactic acid, polyglycolic acid, regenerated collagen, poly-L-lysine, sodium alginate, gellan gum, chitosan, agarose, multilamellar liposomes and many other conventional depot formulations comprise bioerodible or biodegradable materials that can be formulated with biologically active compositions. These materials, when implanted or injected, gradually break down and release the active material to the surrounding tissue. For example, one method of encapsulating PEGylated uricase comprises the method disclosed in U.S. Pat. No. 5,653,974, which is hereby incorporated by reference. The use of bioerodible, biodegradable and other depot formulations is expressly contemplated in the present invention. The use of infusion pumps and matrix entrapment systems for delivery of PEGylated uricase is also within the scope of the present invention. PEGylated uricase can also advantageously be enclosed in micelles or liposomes. Liposome encapsulation technology is well known in the art. See, e.g., Lasic, D, et al., (Eds.) (1995) Stealth Liposomes. Boca Raton, Fla.: CRC Press.

The uricase used in PEGylated uricase can comprise a mammalian uricase amino acid sequence truncated at the amino terminus or the carboxy terminus or both the amino and carboxy termini by about 1-13 amino acids and can further comprise an amino acid substitution at about position 46. The truncated uricase can further comprise an amino terminal amino acid, wherein the amino terminal amino acid is alanine, glycine, proline, serine, or threonine as described in co-pending PCT/US2006/013660 and U.S. provisional application Ser. No. 60/670,573, which are hereby incorporated herein by reference in their entireties.

Phase 3 study was completed as indicated in the Examples. In one aspect of the invention, normalization of uric acid of at least about 3.5 mg/dL was selected as the primary outcome measure to reflect the pharmacodynamic effect of PEGylated uricase. In another aspect of the invention, normalization of uric acid of at least about 4.0 mg/dL was selected as the primary outcome measure to reflect the pharmacodynamic effect of PEGylated uricase. In yet another aspect of the invention, normalization of uric acid of at least about 5.0 mg/dL was selected as the primary outcome measure to reflect the pharmacodynamic effect of PEGylated uricase. In yet another aspect of the invention, normalization of uric acid of at least about 6.0 mg/dL was selected as the primary outcome measure to reflect the pharmacodynamic effect of PEGylated uricase. In another aspect of the invention, normalization of uric acid of at least about 7.0 mg/dL was selected as the primary outcome measure to reflect the pharmacodynamic effect of PEGylated uricase.

It is know that persistently elevated plasma uric acid (PUA) or serum uric acid (SUA) levels result in deposition of uric acid in joints and soft tissues. As the total body burden of uric acid increases, signs and symptoms of gout result, including arthritis, characterized by recurrent painful gout flares, development of tophi and joint deformities with resultant chronic pain/inflammation and consequent loss of physical function.

PEGylated uricase 8 mg q2 wk results in marked decreases in uric acid (PUA and SUA) which is associated with complete resolution of tophi in some patients and decreased tender joint counts. Treatment is also associated with a decrease in the incidence and frequency of gout flares after 3 months of therapy compared with placebo, with continued reductions in flare incidence and frequency with long term administration, up to at least 18 months. These benefits occur in patients with chronic and often severe disease who have no other currently available therapy. Persistent responders are those patients who maintain lowered SUA values in response to repeated PEGylated uricase infusions. Maintenance of lowered SUA values is associated with no or low anti-PEGylated uricase antibody response (titers <2430).

The relationship between measured plasma uric acid (PUA) and serum uric acid (SUA) values was evaluated from serial samples from all patients in phase 3 studies. The rationale for this evaluation related to the use of PUA as the measure for the primary endpoint for all PEGylated uricase trials while SUA is used in clinical practice. The handling and processing of samples for PUA determination is much more involved, and this processing was performed at low temperature and utilized trichloroacetic acid to inactivate and precipitate PEGylated uricase so the drug did not continue to oxidize uric acid. Nevertheless, the experimental results unequivocally show a close correlation between both uric acid values at all time points and irrespective of the uric acid values.

An infusion reaction was defined as any adverse event that occurred during or within 2 hours after the PEGylated uricase or placebo infusion that could not be reasonably attributed to another cause. Although there was protocol-specified infusion reaction prophylatic treatment, infusion reactions occurred in 26% of patient treated with PEGylated uricase q2 wk and 40% with PEGylated uricase q4 wk.

Anti-PEGylated uricase antibodies were observed in about 90% of patients treated with PEGylated uricase. Antibodies at higher titers (>1:2430) were associated with increased clearance of PEGylated uricase and loss of PEGylated uricase activity, but high titers were frequently not detected until some time after uric acid levels were increased, sometimes lagging by several weeks after the loss of PEGylated uricase response. Patients who initially responded to PEGylated uricase and lost response at later time points were referred to as transient responders, in contrast to patients who maintained urate lowering activity of PEGylated uricase throughout the study and were termed persistent responders. The rise in PUA precedes the evidence of higher titers of antibodies.

Patients who developed high antibody titers (but not lower titers) had a high likelihood of loss of PUA response. The evidence of a transient response was clear in all patients by month 4 following initiation of therapy. The clinical effects of immunogenicity are easily detected by regular monitoring of SUA levels during the first few months of therapy. Although those patients who developed higher titer antibodies had a higher incidence of infusion reactions, there was no clear relationship between antibody titer and severity of infusion reactions.

The results herein indicate the development of high titer anti-PEGylated uricase antibodies and anty titer of anti-PEG explains the loss of the SUA/PUA response. In patients that eventually develop higher titers of antibodies to PEGylated uricase there a higher risk of infusion reactions. Importantly, most infusion reactions occur after the loss of SUA/PUA response and, as a result, careful monitoring of SUA can avoid unnecessary dosing and also prevent the majority of infusion reactions. The loss of effect in most transient responders occurs within the first 4 months, so monitoring serum uric acid during that time period is critical. Finally, the loss of effect of PEGylated uricase can frequently occur before the rise in anti-PEGylated uricase antibody titer, so that there is no correlation between the titer of anti-PEGylated uricase antibody, or the presence of any titer anti-PEG antibody, before or at the time of loss of a SUA/PUA response. The lack of association between antibody titer and the SUA/PUA response confirms the ineffectiveness of monitoring antibody titers during PEGylated uricase therapy of patients with treatment failure gout.

EXAMPLE 1

Immunogenicity and Infusion Reaction Profiles of Pegloticase Intravenous Administration at 8 mg Every 2 Weeks Material, Methods and Design of Clinical Study.
Investigational Drug Pegloticase, a PEGylated uricase used in this example, consists of a recombinant mammalian uricase (primarily porcine, with C-terminal sequence from baboon uricase), conjugated with multiple strands of monomethoxy PEG of average molecular weight 10 kDa (10 K mPEG) per subunit of tetrameric enzyme (Kelly S J, et al. J Am Soc Nephrol 2001, 12:1001-1009; and Ganson N J, et al. Arthritis Res Ther 2005, 8(1):R12).
Phase III Study Design.
Patients:

Multi-center (45 sites), replicate, double-blind, placebo-controlled, studies were performed in patients with symptomatic gout.

All patients received an intravenous (i.v.) infusion (pegloticase or placebo) every 2 weeks. Treatment groups consisted of placebo (N=43), pegloticase 8 mg i.v. every 2 weeks (q2 wks) (N=84).

All patients reported a medical history in which allopurinol therapy was contraindicated (e.g., history of hypersensitivity, intolerance, or toxicity) or had not been effective, defined as failure to normalize SUA with ≥3 months allopurinol treatment at the maximum labeled dose (800 mg/day) or at a medically appropriate lower dose based on toxicity or dose-limiting co-morbidity. The major exclusion criteria at entry included: unstable angina, uncontrolled arrhythmia, non-compensated congestive heart failure, uncontrolled hypertension (above 150/95 mmHg), dialysis, organ transplant recipient, pregnancy and other.

For these experiments, all patients discontinued all urate-lowering therapies ≥one week prior to randomization, and refrained from using such agents throughout the study.

All patients received prophylaxis for infusion reactions (IR): oral fexofenadine (60 mg evening prior and immediately before infusion), and acetaminophen (1000 mg) and hydrocortisone IV (200 mg) prior to each infusion. Study medication was administered in 250 mL saline over 2 to 4 hours total infusion time.
Immunogenicity The qualitative and quantitative ELISA assays used for study sample analysis were validated to Good Laboratory Practices following accepted immunology assay guidance (Mire-Sluis et al). Samples for antibody determination using ELISA assays were collected from all patients at baseline and at Weeks 3, 5, 9, 13, 17, 21 and 25 after initiation of treatment with pegloticase or placebo.
Detection of Anti-Pegloticase Antibody.

For determination of total pegloticase antibodies, study samples were diluted 1/30 in assay buffer and assayed using microtiter ELISA plate wells coated with either pegloticase or PEG. A human serum containing pegloticase antibodies was used as a positive control for detection of total pegloticase antibody as well as IgM and IgG antibodies. The combination of rabbit anti-human IgM and IgG was used as secondary antibodies, whereas each individually was employed for assay of IgM and IgG anti-pegloticase antibodies, respectively (Sigma, St. Louis, Mo.)

For these experiments, horseradish peroxidase-conjugated mouse monoclonal antibody to rabbit IgG was used for detection. Microtiter plate wells coated with purified human IgG and IgM served as immunoglobulin positive controls for the binding of anti-human IgG and anti-human IgM secondary antibodies.

Drug interference was determined to be 300 µg/mL which is much higher than the measured circulating pegloticase concentration determined in the study samples. Therefore, circulating pegloticase would not be anticipated to interfere with the measurement of anti pegloticase antibodies.
Properties of the Anti-Pegloticase Antibodies.

For the majority of samples from the phase 3 patients, the antibody response involved both IgM and IgG antibodies.
Detection of Anti-Pegloticase Antibodies.

For these experiments, the anti-pegloticase analysis methodology parallels the general method for the anti-pegloticase antibody assay, with the exception that a surrogate positive control was used for the initial study sample analyses. This positive control consisted of a mixture of mouse monoclonal anti-PEG IgG1 and anti-PEG IgM antibodies, added to pooled human serum and diluted 1/10 in blocker casein in PBS. A human positive control was introduced in the assay towards the end of the study sample analysis. For these experiments, the assay sensitivity was 500 ng/mL and is also reflected in a low false detection rate of 8.6%.

Safety Evaluations—Infusion Reactions.

For these experiments, infusion reactions were defined as any adverse event that occurred during or within 2 hours after the infusion of blinded study medication that could not be reasonably attributed to other causes. Infusion reactions occurred during the infusion of pegloticase and placebo. Signs and symptoms of serious infusion reactions included: dyspnea, hypotension, hypertension, swelling, brochospasm, chest pain, nausea, vomiting and abdominal pain and cramping.

As shown in FIG. 1, at all time points after dosing, the persistent responders in the q2 wk group had lower mean anti-pegloticase antibody titers compared to the transient responders. For example, it was observed that patients with anti-pegloticase antibody titer <1:810 at any time during the study were associated with persistent response. Thus, 68% of the q2 week persistent responders had titers that never exceeded a titer of 1:810. On the other hand, only 23% of the q2 week transient responders had titers <1:810. Therefore, low titer was associated with persistent response.

Anti-Pegloticase Antibody Effects on Pegloticase Pharmacokinetics and Pharmacodynamics.

Figure 2:
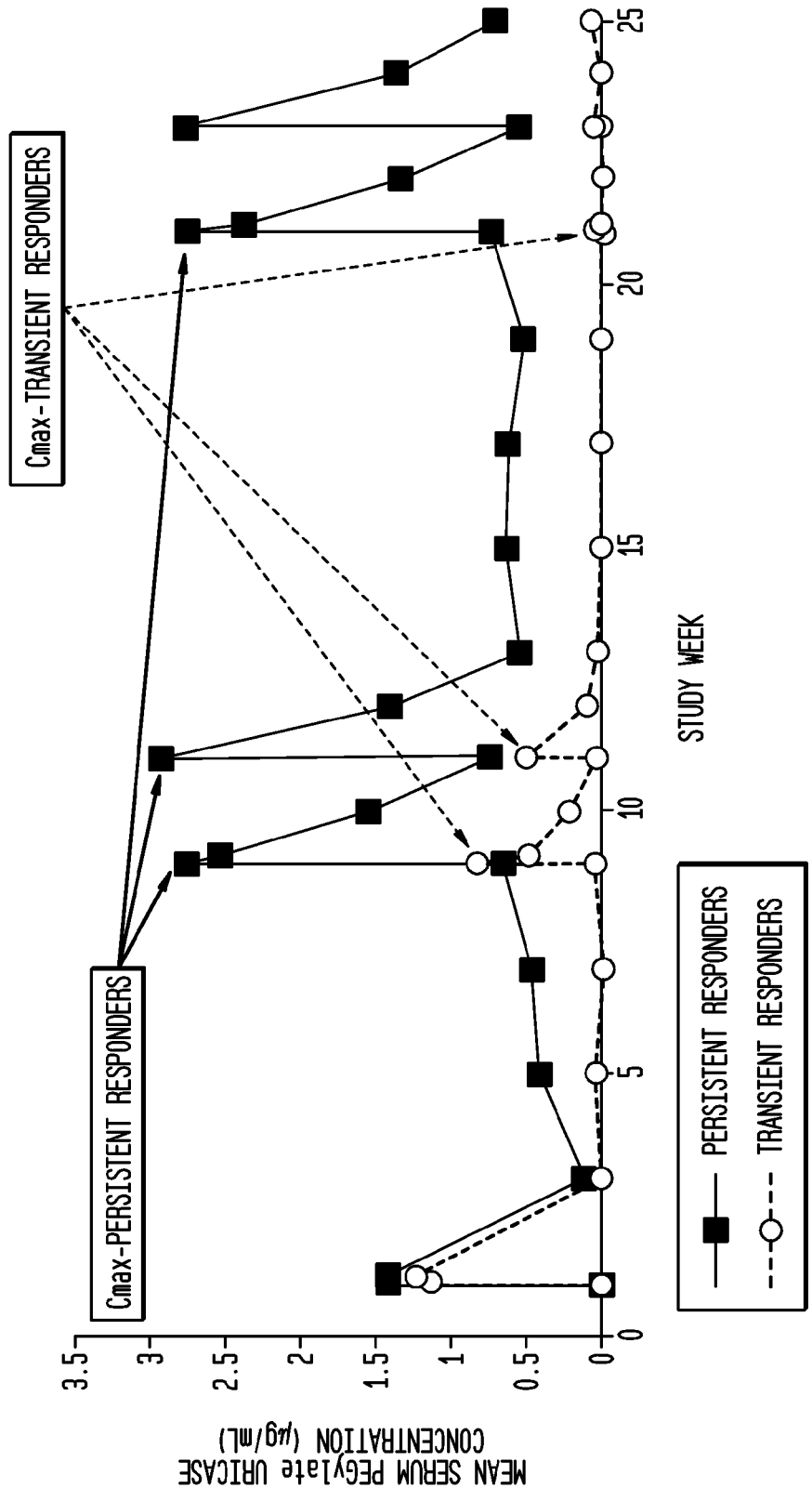
FIG. 2 shows time-concentration profile for pegloticase every 2 week administration.

As shown in FIG. 2, the pharmacokinetics of pegloticase administered every 2 weeks is significantly influenced by the presence of pegloticase antibodies. Persistent responders had higher pegloticase peak concentrations (Cmax) in both groups compared to transient responders. As shown in FIG. 2, transient responders in the q2 wk dose group showed decreased peak pegloticase concentrations after week 3. Further, by week 15, the transient responders had pegloticase concentrations that were below the level of detection (0.6 µg/mL). Persistent responders in the q2 wk group had pegloticase concentrations in the range of 0.5-0.7 µg/mL.

Figure 3:
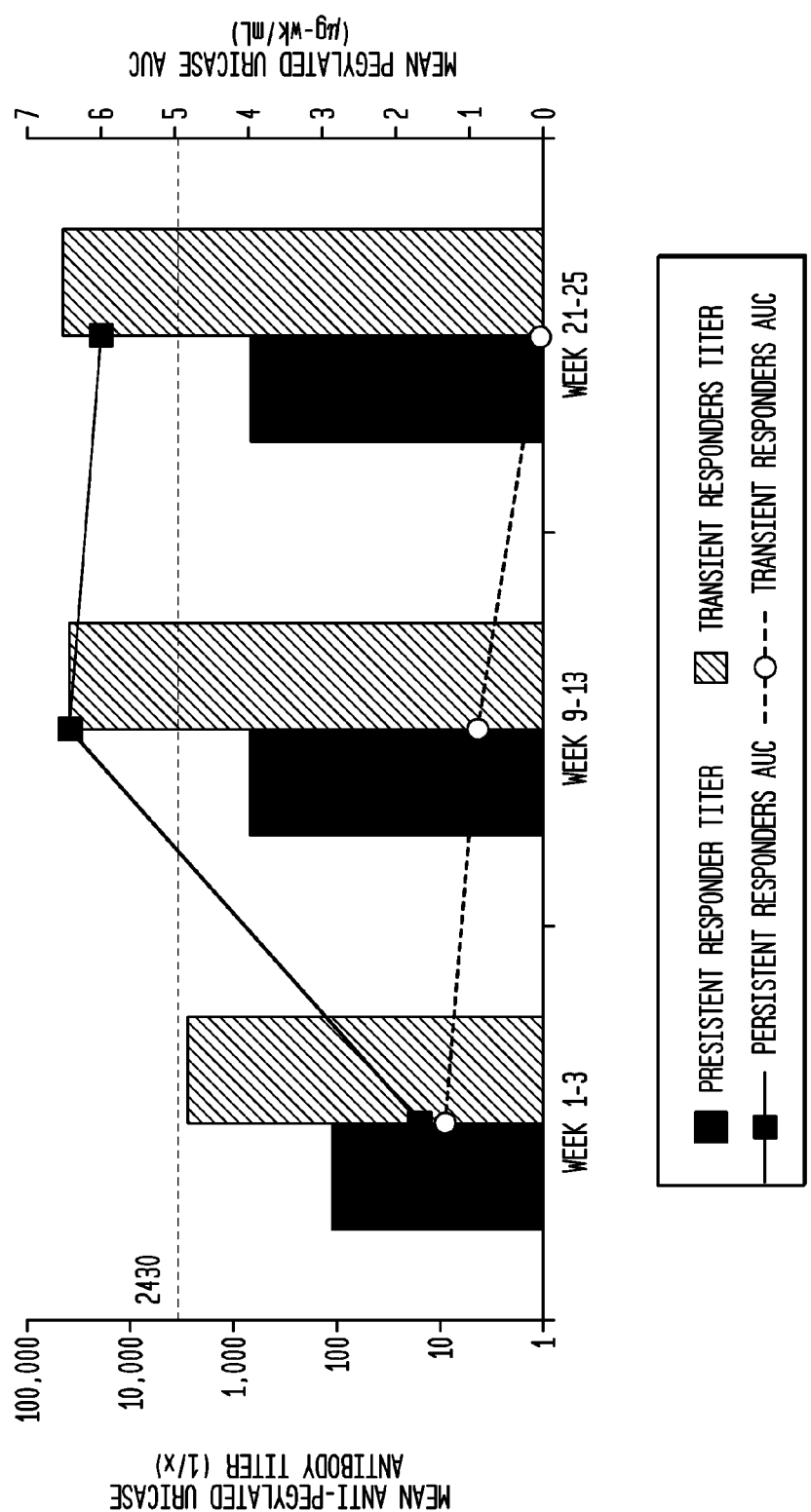
FIG. 3 shows relationship between antibody titer and AUC pegloticase every 2 week administration.

As shown in FIG. 3, in transient responders, the increased anti-pegloticase antibody titers were associated with markedly decreased pegloticase levels as assessed by the area under the time-concentration curve (AUC) compared with the pegloticase levels in the persistent responders. While there is an association between loss of response and development of higher pegloticase titers, loss of response could occur contemporaneously or even before the rise in antibody titer. Therefore, titer determinations are not predictive of loss of pegloticase response.

Anti-Pegloticase Antibody Effects on SUA/PUA Response: SUA/PUA as a Surrogate for Physiologically Relevant Anti-Pegloticase Antibodies.

Figure 4:
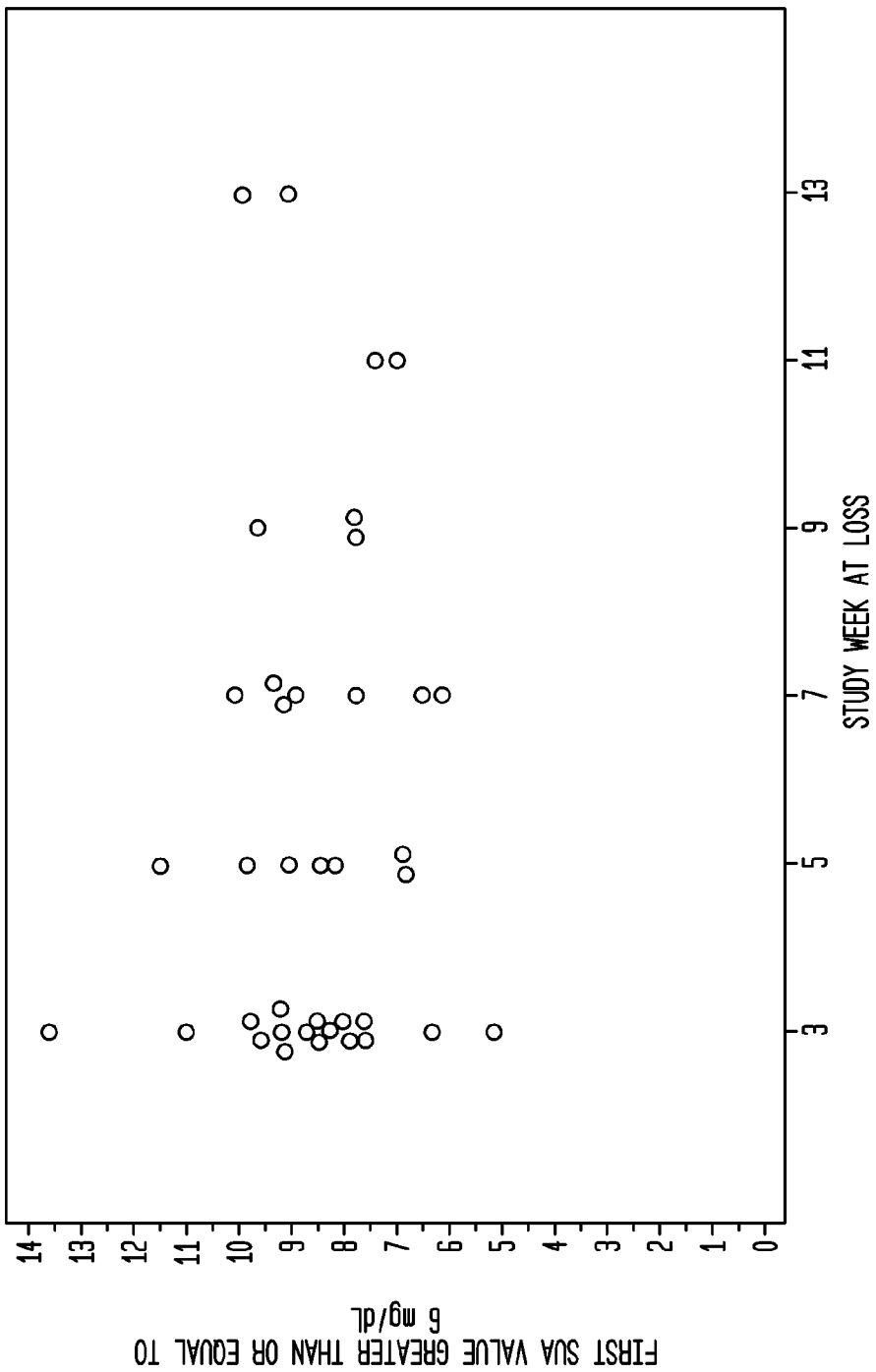
FIG. 4 shows SUA value at first detected loss response pegloticase every 2 weeks.
Figure 5:
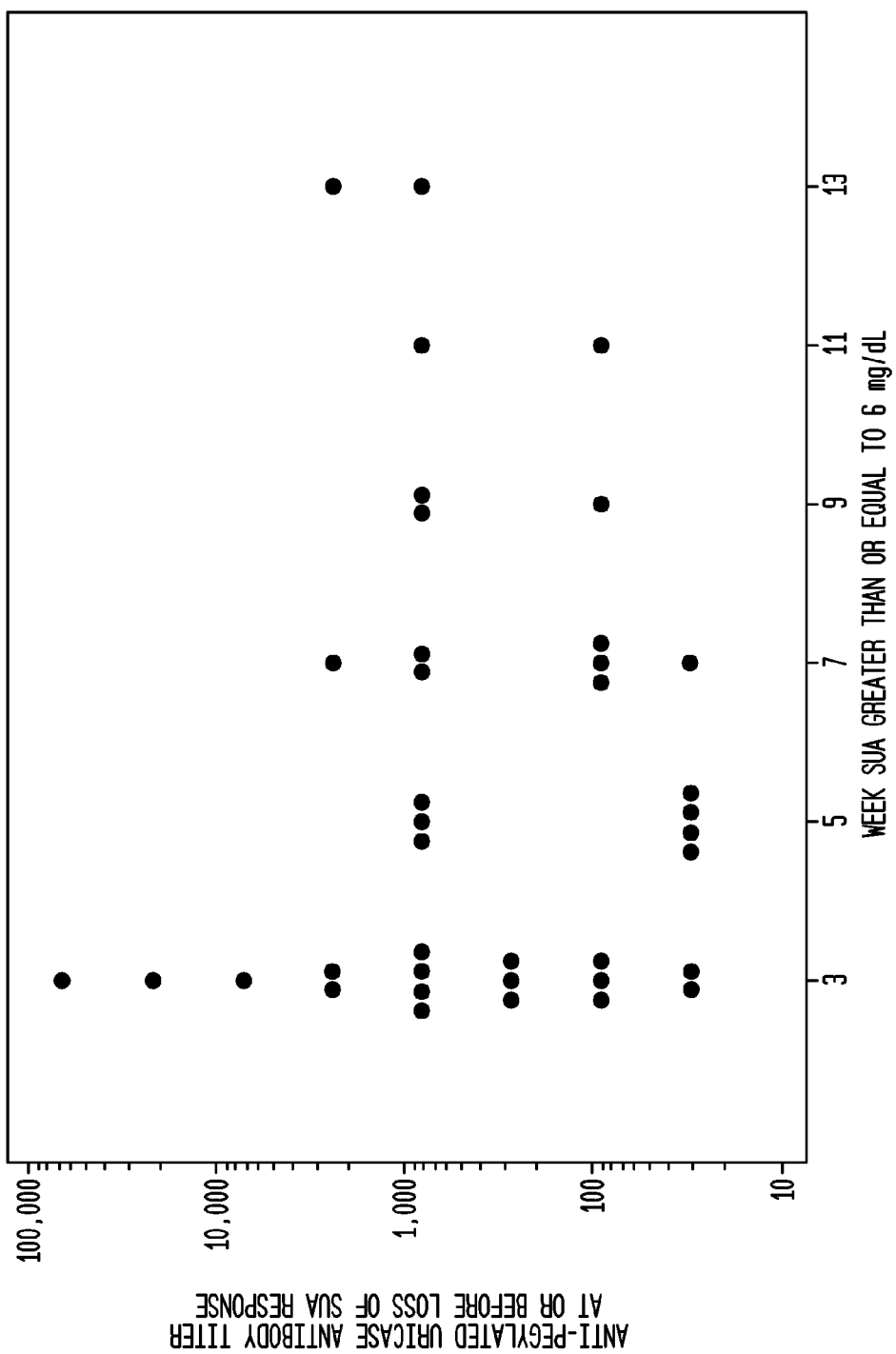
FIG. 5 shows anti-pegylated uricase antibody titer at time of loss of response pegloticase every 2 weeks.

It was further investigated when the SUA increase above 6 mg/dL occurred in the transient responder group following administration of pegloticase 8 mg q2 wks. Each point in the top panel of FIG. 4 represents the first measured SUA value that exceeded the threshold value of 6 mg/dL and the time at which this event occurred for each individual transient responder in the q2 wks group. FIG. 5 shows the corresponding antibody titers that were measured at or before the time of loss of uricase response. However, given that treatment with pegloticase q2 wks results in SUA values that are generally less than 3 mg/dL, the threshold SUA value representing a loss of pegloticase response can be set at an even lower value, for example between about 3.5 mg/dL to about 7 mg/dl. But as the rise in SUA due to loss of pegloticase response is generally rapid, 6 mg/dL is one of the accepted thresholds for control of uric acid by urate lowering drugs. However, 4 mg/dL and 5 mg/dL can be used successfully in these experiments as a threshold value for control of uric acid by urate lowering drugs.

At the time of loss of SUA normalization in the q2 wk group, i.e., when SUA exceeded 6 mg/dL, there was a wide range of anti-pegloticase antibody titers so that there appeared no threshold antibody titer that corresponded to this loss of response, as shown in FIG. 5. Specifically, at the time of loss of urate response, mean anti-pegloticase antibody titers were 1:3032 for the q2 wk group as compared to a mean highest titer of 1:686 for the q2 wk persistent responders.

Infusion Reaction and Loss of SUA Normalization.

Most patients (90.9%) had infusion reactions after pegloticase activity was lost, that is when SUA values were greater than or equal to 5 mg/dL (Table 1).

TABLE 1

SUA Category At Time of Infusion Reaction in Patients Receiving pegloticase Every 2 Weeks

| SUA Category | pegloticase 8 mg q2 wk n/N (%) | Placebo n/N (%) |
|---|---|---|
| Number of Patients with IR when SUA ≥ 5 mg/dL | 20/22 (90.9) | 2/43 (4.7) |
| Number of Patients with IR when SUA < 5 mg/dL | 1/22 (4.5) | 0 |
| Number of Patients with IR at First Dose | 1/22 (4.5) | 0 |

As shown in Table 1, in q2 wk group, 90.9% of infusion reactions would have been prevented if pegloticase therapy was discontinued at the time point when SUA≥5 mg/dL.

In summary, anti-pegloticase antibodies have direct effects on the pharmacokinetic and pharmacodynamic properties of pegloticase and explain the transient effect of pegloticase in the patients who develop physiologically-relevant antibodies. Although the increased clearance of pegloticase with the resultant loss of SUA/PUA response is mediated by anti-pegloticase antibodies, the initiation of increased clearance does not correlate with the anti-pegloticase antibody titer. Therefore, measurement of anti-pegloticase antibody titers is not predictive of the loss of the SUA/PUA response, whereas monitoring SUA/PUA is a very good surrogate for measuring the development of anti-pegloticase antibodies that cause increased clearance of administered pegloticase. Most importantly, monitoring SUA values, particularly during the first 4 months after initiating treatment with pegloticase, and stopping treatment with pegloticase when SUA values rise to levels greater than about 3.5 to 4 mg/dL is a simple method for identifying individuals who lose response to pegloticase and are at higher risk of experiencing an infusion reaction.

EXAMPLE 2

Immunogenicity and Infusion Reaction Profiles of Phase III Clinical Study: Pegloticase Intravenous Administration at 8 Mg Every 4 Weeks Clinical Study Using Infusion of Pegloticase.

A multicenter, randomized, double-blind placebo controlled clinical study was carried out as indicated in Example 1 above. Patients with hyperuricemia and gout received pegloticase 8 mg intravenously every 4 weeks (N=84) or placebo (N=43). Treatment was administered for 24 weeks.

Patients must have discontinued any uric acid-lowering agents for at least one week prior to receiving study drug, and refrain from using such agents throughout the study.

Anti-pegloticase antibodies were detected in 88% of patients in the pegloticase 8 mg q4 wk and in only 15% of the placebo group.

Figure 6:
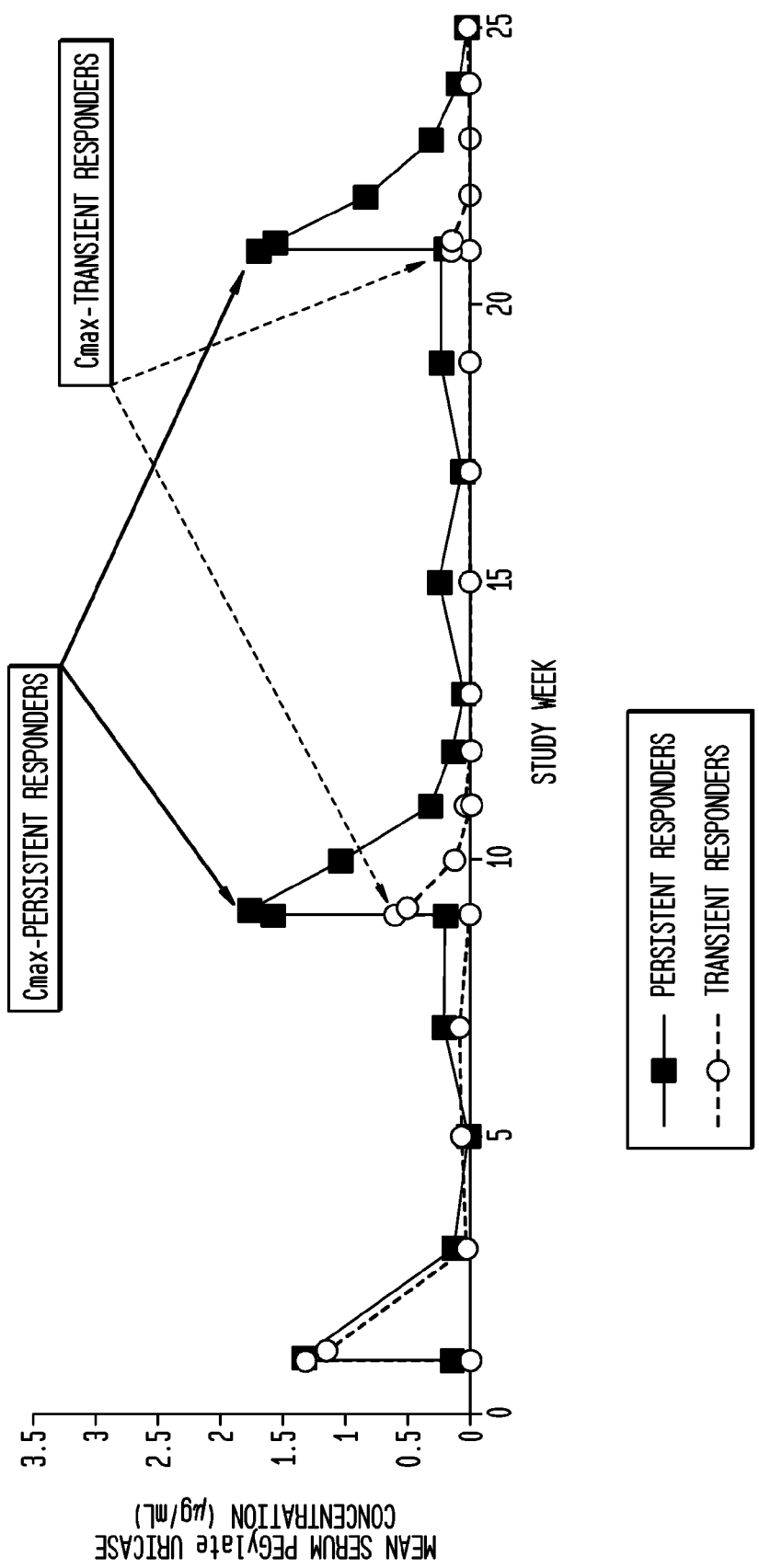
FIG. 6 shows time-concentration profile for pegloticase every 4 week administration.

As shown in FIG. 6, the pharmacokinetics of pegloticase administered every 4 weeks is significantly influenced by the presence of anti-pegloticase antibodies. Persistent responders had higher pegloticase peak concentrations (Cmax) in both groups compared to transient responders.

Table 2 shows that most patients (76.5%) who had an infusion reaction had SUA values at or above 6 mg/dL at the time the infusion reaction occurred. These infusion reactions could have been prevented if pegloticase was discontinued at the time point that SUA values were 6 mg/dL. Four patients had infusion reactions when SUA was less than 6 mg/dL and four patients who had an infusion reaction at first dose; none of these infusion reactions could have been prevented by monitoring SUA values. \

TABLE 2

SUA Category at Time of Infusion Reaction in Patients Receiving pegloticase Every 4 Weeks

| SUA Category | pegloticase 8 mg q4 wk n/N (%) | Placebo n/N (%) |
|---|---|---|
| Number of Patients with IR when SUA ≥ 6 mg/dL | 26/34 (76.5) | 2/43 (4.7) |
| Number of Patients with IR when SUA < 6 mg/dL | 4/34 (11.8) | 0 |
| Number of Patients with IR at First Dose | 4/34 (11.8) | 0 |

What is claimed is:

1. A method of treating a patient suffering from gout having a serum uric acid (SUA) level of 6 mg/dl or less, and reducing the incidence of infusion reaction in said patient, the method comprising:
    administering to said patient, a PEGylated uricase at a dosage of 8 mg every two weeks;
    after a first period of time, determining the SUA level of said patient, and
    if said SUA level of the patient is maintained below 6 mg/dl, continuing said administration of PEGylated uricase at a dosage of 8 mg every two weeks, whereas if said SUA level of the patient is above 6 mg/dl, discontinuing said administration thereby reducing the incidence of infusion reaction in said patient, wherein said patient previously received ineffective allopurinol therapy or has a medical history in which allopurinol therapy is contraindicated.

2. The method according to claim 1, wherein said SUA level is determined after 24 hours but within 2 weeks of said administering.

3. The method according to claim 1, wherein said first period of time is two weeks.

4. The method according to claim 1, wherein said gout is refractory.

5. The method according to claim 1, wherein said gout is chronic or tophaceous.

6. The method according to claim 1, wherein said PEGylated uricase is administered intravenously.

* * * * *